ns. <br>
United States Patent [19]

Rosicky

[11] 3,937,613
[45] Feb. 10, 1976

[54] DEVICE FOR THE DETERMINATION OF CHLORINE IN THE WATER OF SWIMMING POOLS

[75] Inventor: Jan Rosicky, Lindfield, Australia

[73] Assignee: Alpha Chemicals (Australia) Pty. Limited, Australia

[22] Filed: Apr. 4, 1975

[21] Appl. No.: 565,297

[52] U.S. Cl............. 23/253 TP; 23/230 R; 260/573
[51] Int. Cl.² ................. G01N 31/22; G01N 33/18
[58] Field of Search...... 23/253 TP, 230 R; 260/573

[56] References Cited
UNITED STATES PATENTS

| | | | |
|---|---|---|---|
| 3,122,420 | 2/1964 | Rebar, Jr. et al. | 23/253 TP |
| 3,329,486 | 7/1967 | Rupe | 23/253 TP |
| 3,701,633 | 10/1972 | Davis | 23/253 TP |
| 3,811,840 | 5/1974 | Bauer et al. | 23/253 TP |
| 3,843,325 | 10/1974 | Schmitt et al. | 23/253 TP X |
| 3,873,269 | 3/1975 | Krafflzyk et al. | 23/253 TP X |

OTHER PUBLICATIONS

Ciaccio, "Water & Water Pollution Handbook," Vol. 3; Marcel Dekker, Inc.; N.Y. 1972, pp. 1178–1180.

*Primary Examiner*—Morris O. Wolk
*Assistant Examiner*—Arnold Turk
*Attorney, Agent, or Firm*—Ladas, Parry, Von Gehr, Goldsmith & Deschamps

[57] ABSTRACT

Para-ethyl-oxyethylamino-aniline or one of its salts is employed as a reagent for testing the presence of chlorine in the water of swimming pools. The reagent dissolved or dispersed in a polypropylene-glycol ethoxylate is coated on to a support. When the coated support is stirred into the water a pink color develops in the water if chlorine is present and the intensity of the color can be used to gauge quantitatively the amount of chlorine present.

9 Claims, No Drawings

DEVICE FOR THE DETERMINATION OF CHLORINE IN THE WATER OF SWIMMING POOLS

BACKGROUND OF THE INVENTION

The determination of the chlorine content in water, especially in the water of swimming pools is an important and widely used control reaction. The most current method used for this purpose is the reaction between chlorine and ortho-tolidine (OTO), a yellow color being produced by oxidation of the molecule by chlorine. The intensity of the resulting coloration in a given volume of the tested water is compared with an empirically established color scale, thus giving a quantitative estimate of the chlorine content. The sensitivity of the reaction is high, but the pale yellow shade produced by concentrations under 0.5 parts per million of chlorine renders an exact estimation a little difficult.

The solutions of OTO are sufficiently stable so that this form of the reagent, i.e. solution, can be used for an easy testing in small private swimming pools.

However, an objection has been raised against the use of OTO for this purpose. Its cancerogenic activity has been experimentally established and this fact has cast a shadow on its wide-spread use. Attempts to replace OTO, which gives a highly sensitive and specific reaction with chlorine, by another substance have not been very successful, so far. The only substance, discovered by Palin, which has found some use for satisfactory chlorine determinations is assym.diethyl-paraphenylene-diamine (DPD). A certain drawback is its strongly allergenic character which necessitates a certain caution in its manipulation. The commercial form is DPD tablets sealed in a metallic foil. They are used in connection with the Lovibond comparator. This makes their use considerably more expensive than the use of OTO in the current cheap test kits.

It has now been found that, under certain conditions, which are the object of the present patent application, another member of the phenylene-diamine group can be advantageously used for routine chlorine testing. It does not possess the toxicity of DPD and its allergenicity is, under the conditions of the reaction, insignificant. The chemical composition is para-ethyl-oxyethylamino-aniline (EOAA), and it is used preferably in the form of its salts. It is generally more soluble than DPD, very easily oxidizable and its molecule is much more rapidly destroyed than that of DPD. These properties preclude the use of the base and its salts in solutions similar to those of OTO. The stability of EOAA salts in various organic solvents (e.g., alcohols, acetone, glycols) or acidic solutions in water (even in the presence of complexing agents) is of the order of several minutes to about one month in a closed container. A repeated exposure of the solutions to air by opening the containers for sampling, cuts down the stability still more, so that a stable EOAA reagent cannot be prepared in this way. The only exception is the solution of EOAA in glycerine (BP quality) which keeps stable over one year and lends itself to possible practical use.

It has also now been found that the salts of paraethyl-oxyethylamino-aniline (EOAA) can be brought, as solids, into a form which is most practical and useful for chlorine determinations and which is, under appropriate preserving conditions quite stable. The form of tablets has not been found very practical because of the relatively slow disintegration of the tablets and the necessity of mixing the tested sample.

SUMMARY OF THE INVENTION

According to the present invention, the EOAA, preferably in the form of its salts is fixed as a layer on a support which can be paper, plastic, fabric, ceramic, glass, wood etc. The shape of the support is preferably that of a strip or a thin rod, so that it can be used easily for mixing the tested liquid. The shape of the support can also be, for example, that of little squares, rectangles, round platelets which can be immersed into the tested liquid.

The mode of fixation of EOAA on the surface of the support is of essential importance. On porous material like paper it can be effected by imbibition of the material with a solution of an EOAA salt. However, the release of EOAA into solution, in this case, is not ideal and also the stability is not satisfactory. It has been found that layers of EOAA on porous and non-porous material of excellent desirable properties can be obtained by the use of a dispersing agent in which the EOAA is dissolved or dispersed, which sticks well to the carrier and which, at the same time, forms a protective layer against oxidation by air. The dispersing agent must be of such a nature that it is extremely easily soluble in water and does not react with chlorine by itself, thus eliminating the danger of a competition for chlorine with EOAA.

It has been found, on the basis of very numerous trials, that the best dissolving and dispersing agents for this purpose are from the group of polymeric substances of high molecular weight. The most suitable representatives of this group are non-ionic high molecular propyleneglycol ethoxylates. (PGE). Best results have been obtained by use of polypropylene-glycol 1750 condensed with about 150 molecules of ethyleneoxide of an average molecular weight of 8300 (PGE 8300). Some of them are easily soluble in various organic solvents, like methanol, ethanol and others, and are very soluble in water. Some of them dissolve EOAA directly, when molten. They do not influence the chlorine content even when present in large amounts. The layers of EOAA prepared with these polymers show a very good stability, and the reaction of such layers with chlorine in water is immediate and complete. Other types of polymers like gelatin, polyvinylalcohol, polyvinylacetate do not give satisfactory results. They either react with chlorine (gelatin) or do not release EOAA properly and do not stabilise it to the desired degree. The use of the dispersing agents from the group of non-ionic polymers represents a new original finding and makes possible a practical and safe use of EOAA for routine determination of chlorine in swimming pools. The most practical form are strips of e.g. polyvinylchloride, polystyrene cellulose acetate or other inert plastic of the dimensions e.g. 75 mm by 6 mm carrying on one end a layer of EOAA in a polymeric substance as mentioned above. For performing the reaction the strip, held by hand, is immersed with the layer-end into the tested water in the test tube or cuvette of the test kit, shortly stirred and taken out. The forming of the colour in the tested water is immediate and its depth of colour throughout the whole length of the tube quite regular, without shaking the kit or touching the solution with fingers. The intensity of the pink coloration is compared with a printed colour scale adjacent to the cuvette.

DESCRIPTION OF THE PREFERRED EMBODIMENTS

The use of EOAA opens still further possibilities how to modify the colour reaction by chlorine. The oxidation product of EOAA produced by chlorine is capable of coupling with certain groups of chemicals e.g. those carrying phenolic functions in their molecules or active methylene groups and thus forming new dyestuffs, e.g., blue, magenta, yellow. Red or yellow shades may be useful for modifying the original pink shade of oxidized EOAA, should it be desirable for some purposes. The blue colour may probably be of great interest in chlorine determinations using a blue comparison scale. A strip with a layer prepared from EOAA and 1-naphtol or 1-oxynaphthalin-2-sulphonic acid or preferably 2-4 dichloro-1-naphthol and a polymeric substance gives with chlorine a blue colour. The coupling reaction depends to some extent on the pH of the reacting liquid. In order to create the desirable pH in the tested sample of water a layer containing buffers or pH modifiers can be fixed on the strip. In this way the coupling reaction proceeds always under similar conditions and gives constant results even if the pH of the sample varies. The buffers have to accelerate the coupling reaction and to fix it at the desired degree. A too high pH may start a coupling reaction going beyond the proportion corresponding to the chlorine content. This has to be avoided. In that respect the lithium hydroxide and preferably the lithium carbonate have given particularly good results as mild pH modifiers.

Another possibility that is offered by the use of EOAA strips is the determination both of free and of residual chlorine. This needs a normal strip with a EOAA layer and another strip where, besides the EOAA layer a layer containing an iodide, e.g. potassium idodide, dissolved in the non-ionic polymer is fixed. The difference of the indicated chlorine content between the two strips indicates the amount of fixed chlorine. The principle of the device destined for measurement of the chlorine content in water by a colour reaction between chlorine and EOAA having been explained in the above description some examples of their preparation are given:

EXAMPLE 1

Ashless filter paper is impregnated with a 2% solution of EOAA in a 20% methanolic solution of PGE and is dried rapidly in a stream of hot air. The dry paper can be cut in various shapes, e.g., little squares. They are preserved in a closed tube. For use, they are immersed into the tested solution. They can also be fixed to one end of a plastic or wooden strip for better handling.

EXAMPLE 2

A sheet of white polyvinylchloride, 0.2 mm thick, of the dimensions 75 mm by 300 mm is dipped on one of the larger sides into a solution of 3 gm EOAA in 100 ml of methanol and 20g of PGE 8300 and dried rapidly in a stream of hot air. The breadth of the layers is 20 mm. The sheet is then cut into strips 75 mm long and 6 mm broad. Instead of dipping the sheet into solution the active layer can also be made by painting or printing it. A solution of 0.3 gm EOAA in 10 ml of a 40% solution of PGE 8300 is painted with a brush to form on one of the longer sides of the sheet a layer 30 mm broad. The sheet is dried and cut as above. It is advantageous to use a sheet with one matt side for the painting or printing method, the layer being put thereon.

EXAMPLE 3

A solution consisting of primary and secondary potassium and sodium phosphates forming a buffer of pH 6.5 and a PGE is painted in the centre of a polyvinylchloride or acetylcellulose sheet, forming a 20 mm layer and is dried. When dry, a solution of 0.3 gm EOAA and 0.29 gm 2- 4-dichloro-1-naphthol in a 40% solution of PGE 8300 in methanol is used for painting of the active layer on one of the longer sides of the sheet. The sheet is dried and cut as above. Instead of painting an active layer composed of EOAA and 2-4-dichloro-1-naphthol dispersed in the same solution, it is possible to fix the EOAA and the 2-4-dichloro-1-naphthol in two separate layers.

EXAMPLE 4

On the edge of a longer side of white, rectangular polystyrene sheet a layer consisting of 0.4 gm of EOAA and 2 gm of potassium iodide in a 40% solution of PGD 8300 in methanol is painted and dried rapidly. It is also possible to paint two separate layers, one containing EOAA, the other the iodide. This type of strip is used for determination of free and total chlorine in the water of swimming pools.

In a similar way various chemicals can be fixed on the strips serving for various purposes of the analysis.

EXAMPLE 5

A white rectangular PVC or acetylcellulose sheet is dipped with one of the longer sides into a solution of 3 gm EOAA in 100 ml of a 40% solution of PGE 8300 in methanol and dried rapidly. Then the other longer side is dipped into a solution of 0.2 gm of the sodium salt of Phenol Red in 100 ml of a 20% solution of the same dispersant and dried rapidly. After cutting the sheet in 6 mm broad strips, strips are obtained having active layers on both sides. They can be used for both purposes, first determination of pH with one end and then determination of chlorine with the other end, thus simplifying the manipulation.

EXAMPLE 6

Sheets of polystyrene 0.2 mm thick, 300 mm long and 75 mm broad are used as a support for the active EOAA layer. A solution of 0.3g of EOAA sulphate and of 0.29g 2-4-dichloro-1-naphthol in 10 ml of a 30% methanolic solution of PGE 8300 is painted with a brush on one of the longer sides of the rectangle to form a layer 15 mm broad. It is then dried rapidly in a stream of hot air. On the same side of the sheet about 10 mm away from the dyestuff layer and going parallel to it a 5 mm broad layer of a suspension of 0.2 g lithium carbonate in 5 ml of a methanolic 30% solution of PGE 8300 is painted and dried rapidly. The sheets are cut to form strips 75 mm long and 6 mm wide. Every strip has on one end a 15 mm broad layer of the reagent dyestuffs and a separate parallel layer of lithium carbonate acting as a pH modifier. When immersed into the tested sample and slightly stirred the strip produces in the sample a blue colour, permitting an immediate reading on the blue colour scale.

The use of strips based on EOAA represents a real progress in the routine determination of chlorine in swimming pools. They replace the potential cancerogen OTO and DPD tablets which are a potential allergenic substance, by a much safer product. They are stable and avoid a certain difficulty which always is present when solutions are handled, drops counted, the test tube to be closed with fingers and shaken. The strip is just taken out of the tube, where it is preserved, dipped into the test tube or cuvette, lightly stirred and discarded. The colour produced in the tested sample of water in the cuvette is immediately compared with the colour scale in the kit. Since it is possible to fix on the strips other reagents (potassium iodide, buffers, indicators) they can be very versatile in their use. Thus, the strips can replace completely all solutions in the testing kits.

What I claim is:

1. A device for the determination of chlorine in the water of swimming pools comprising a substrate suitably shaped for immersion into a sample of the water to be tested carrying on at least a portion of its surface a layer of a composition comprising an active reagent, selected from the group consisting of para-ethyl-oxyethylamino-aniline and the salts thereof, dissolved or dispersed in a polypropylene-glycol ethoxylate.

2. A device according to claim 1 wherein the polypropylene-glycol ethoxylate is polypropylene-glycol 1750 condensed with about 150 molecules of ethylene oxide of an average molecular weight of 8,300.

3. A device according to claim 1 wherein the substrate is a non-reactive plastic in a shape selected from the group consisting of strips, thin rods and platelets.

4. A device according to claim 1 wherein a coupler substance capable of coupling with the oxidation product resulting from the oxidation of para-ethyl-oxyethylamino-aniline by chlorine and thus forming a new dyestuff is incorporated in the layer on the substrate.

5. A device according to claim 1 wherein a coupler substance capable of coupling with the oxidation product resulting from the oxidation of para-ethyl-oxyethylamino-aniline by chlorine and thus forming a new dyestuff is fixed on the substrate in a layer separate from that containing the para-ethyl-oxyethylamino-aniline.

6. A device according to claim 4 wherein the coupling substance is selected from the group consisting of 1-naphthol and derivatives thereof.

7. A device according to claim 1 having fixed to the substrate at least one layer in addition to the active reagent layer containing a substance selected from the group consisting of buffers and pH modifiers.

8. A device according to claim 7 wherein the pH modifier is lithium carbonate.

9. A device according to claim 1 wherein a layer of an iodide capable of liberating fixed chlorine in the tested sample is adhered to the said substrate.

* * * * *